US009227085B2

(12) United States Patent
Ma et al.

(10) Patent No.: US 9,227,085 B2

(45) Date of Patent: Jan. 5, 2016

(54) INCLUDING FIDUCIAL MARKERS IN RADIATION THERAPY PLANNING TO FACILITATE REAL-TIME POSITION MONITORING DURING TREATMENT DELIVERY

(75) Inventors: Yunzhi Ma, Mountain View, CA (US); Paul J. Keall, Greenwich (AU); Lei Xing, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1311 days.

(21) Appl. No.: 12/932,666

(22) Filed: Mar. 2, 2011

(65) Prior Publication Data

US 2015/0265851 A1 Sep. 24, 2015

Related U.S. Application Data

(60) Provisional application No. 61/339,326, filed on Mar. 2, 2010.

(51) Int. Cl.

*G21K 1/02* (2006.01)
*A61N 5/10* (2006.01)
*A61B 19/00* (2006.01)

(52) U.S. Cl.

CPC .............. *A61N 5/1031* (2013.01); *A61B 19/54* (2013.01); *A61N 5/1036* (2013.01); *A61N 5/1037* (2013.01); *A61N 5/1045* (2013.01); *A61N 5/1077* (2013.01); *A61N 2005/1035* (2013.01)

(58) Field of Classification Search

CPC .............. A61N 5/1031; A61N 1/0534; A61N 1/36082; A61N 1/0539; A61N 1/36135; A61N 1/36146; A61N 2005/1087; A61N 5/1039; A61N 5/1042; A61N 2005/1041; A61N 5/1007; A61N 5/1047; A61N 1/36025; A61N 1/36067; A61N 1/3613; A61N 5/1064; A61N 2005/1035; A61N 5/1036; A61N 5/1045; A61N 5/1077; A61N 5/1049; A61N 5/103; A61N 2005/1091; A61N 5/1017; A61N 5/10; A61N 5/1037; A61N 2005/105; A61N 2005/1061; A61N 2005/1097; A61N 5/1067; A61N 5/1084; A61N 2005/108; A61B 19/54

USPC ...................................................... 378/65, 64

See application file for complete search history.

(56) References Cited

U.S. PATENT DOCUMENTS

| | | | | |
|---|---|---|---|---|
| 5,418,827 A * | 5/1995 | Deasy et al. | 378/65 |
| 5,602,892 A * | 2/1997 | Llacer | 378/65 |
| 5,740,225 A * | 4/1998 | Nabatame | 378/65 |
| 5,859,891 A * | 1/1999 | Hibbard | 378/62 |
| 6,038,287 A * | 3/2000 | Miles | 378/117 |
| 6,411,675 B1 * | 6/2002 | Llacer | 378/65 |
| 2005/0207531 A1 * | 9/2005 | Dempsey et al. | 378/65 |

* cited by examiner

*Primary Examiner* — Irakli Kiknadze

(74) *Attorney, Agent, or Firm* — Lumen Patent Firm

(57) ABSTRACT

An inverse planning method that is capable of controlling the appearance of the implanted fiducial(s) in segmented IMRT fields for cine MV or combined MV/kV image-guided IMRT is provided. The method for radiation treatment includes computing a radiation treatment plan and delivering beams to a target in accordance with the radiation treatment plan, where computing the radiation treatment plan includes introducing a penalty in an inverse planning objective function optimization calculation to discourage or avoid blockage of one or more fiducials in optimized multi-leaf collimator (MLC) apertures.

12 Claims, 13 Drawing Sheets

INCLUDING FIDUCIAL MARKERS IN RADIATION THERAPY PLANNING TO FACILITATE REAL-TIME POSITION MONITORING DURING TREATMENT DELIVERY

CROSS-REFERENCE TO RELATED APPLICATIONS

This application claims priority from U.S. Provisional Patent Application 61/339,326 filed Mar. 2, 2010, which is incorporated herein by reference.

STATEMENT OF GOVERNMENT SPONSORED SUPPORT

This invention was made with Government support under contract 5R01CA104205 awarded by National Cancer Institute, and under contract W81XWH05-1-0041 awarded by Department of Defense. The Government has certain rights in this invention.

FIELD OF THE INVENTION

The current invention relates to enhancing the visibility of implanted fiducials in the segmented fields of intensity-modulated radiation therapy (IMRT) and volumetric modulated arc therapy (VMAT).

BACKGROUND OF THE INVENTION

In current LINAC-based IMRT, a critical component that is missing is the real-time monitoring of the tumor position. Furthermore, a treatment verification system capable of documenting the beam targeting and preventing geographic misses is not available, especially for modern modalities such as gated delivery and therapy relying on MLC-based tumor tracking. A strategy of using combined MV treatment beam and on-board kV imaging system for real-time tracking of fiducial markers has been proposed recently. When the fiducials are inside both kV and MV beams, the geometric accuracy of the system is found to be on the order of 1 mm in all three spatial dimensions.

In using the treatment MV beam for on-line imaging, a practical difficulty is that the fiducials may be partially or completely blocked by the MLC at a certain segment (segments) of an IMRT delivery. A potential solution to the problem is to design the IMRT plan in such a way that all or some of the implanted fiducials are inside the segmented IMRT fields provided that the final dose distribution is not compromised excessively.

"Seeing" the fiducial is a general requirement whenever the fiducials need to be monitored during the beam-on time. This issue arises not only in recently available time-resolved radiation therapy, such as respiration-gated IMRT and four-dimensional (4D) IMRT, but possibly also in conventional 3D IMRT where it may be desirable to ensure that the target volume remains within a prespecified tolerance.

What is needed in the art is a method of introducing a soft or hard penalty in an inverse planning calculation to discourage or avoid the blockage of the implanted fiducials in optimized multi-leaf collimator (MLC) segments.

SUMMARY OF THE INVENTION

To address the needs in the art, a 4D inverse planning method that is capable of controlling the appearance of the implanted fiducial(s) in segmented IMRT fields for cine MV or combined MV/kV image-guided IMRT is provided. The method for radiation treatment includes computing a radiation treatment plan and delivering beams to a target in accordance with the radiation treatment plan, where computing the radiation treatment plan includes introducing a penalty in an inverse planning objective function optimization calculation to discourage or avoid blockage of one or more fiducials in optimized multi-leaf collimator (MLC) apertures.

According to one aspect of the invention, the penalty comprises a hard penalty or a soft penalty, wherein the hard penalty avoids blockage of the fiducial, wherein the soft penalty discourages blockage of the fiducial.

In a further aspect of the invention, the fiducials can include an implanted fiducial, a skin marker, a tissue feature point, or a tissue region.

In another aspect of the invention, the MLC aperture includes segment aperture shapes that conform to a projection of the target in a beam's eye view of the delivery beam, where the shapes are optimized according to a space and phase of a breathing cycle in a patient.

In yet another aspect of the invention, motion of the fiducials is discretized into phase-segments. In one aspect, for a given gantry angle θ and phase p, a weight $w_{\theta p}$ is provided for a phase-segment, where the radiation treatment plan optimizes shapes and weights of all the MLC aperture shapes. Further, the MLC aperture includes MLC segments, where a calculated dose distribution is a function of the MLC aperture shapes and weights of all the MLC segments. In another aspect, a radiation dose provided to a voxel includes a superposition of the radiation doses and phase-segments from all the MLC segments, wherein the dose is determined by summing a contribution from each the MLC segment for each the beam.

According to a further aspect of the invention, the penalty is dedicated to a voxel with a dose higher than a designated upper bound or dedicated to a voxel with a dose lower than a designated lower bound According to another aspect of the invention, the inverse planning objective function is optimized using a simulated annealing (SA) technique, where in each iteration of the SA a trial change of the aperture and trial change of a weight of the penalty is introduced, where the trial change is accepted or rejected according to a probability determined by an SA probability and whether an MLC segment blocks the fiducial or not.

In another aspect of the invention, the inverse planning objective function is optimized using an optimization function.

In a further aspect of the invention, the inverse planning objective function is a 4D inverse planning objective function.

In a further aspect of the invention, the penalty has a value in a range of 0 to 1.

DETAILED DESCRIPTION

Figure 1:
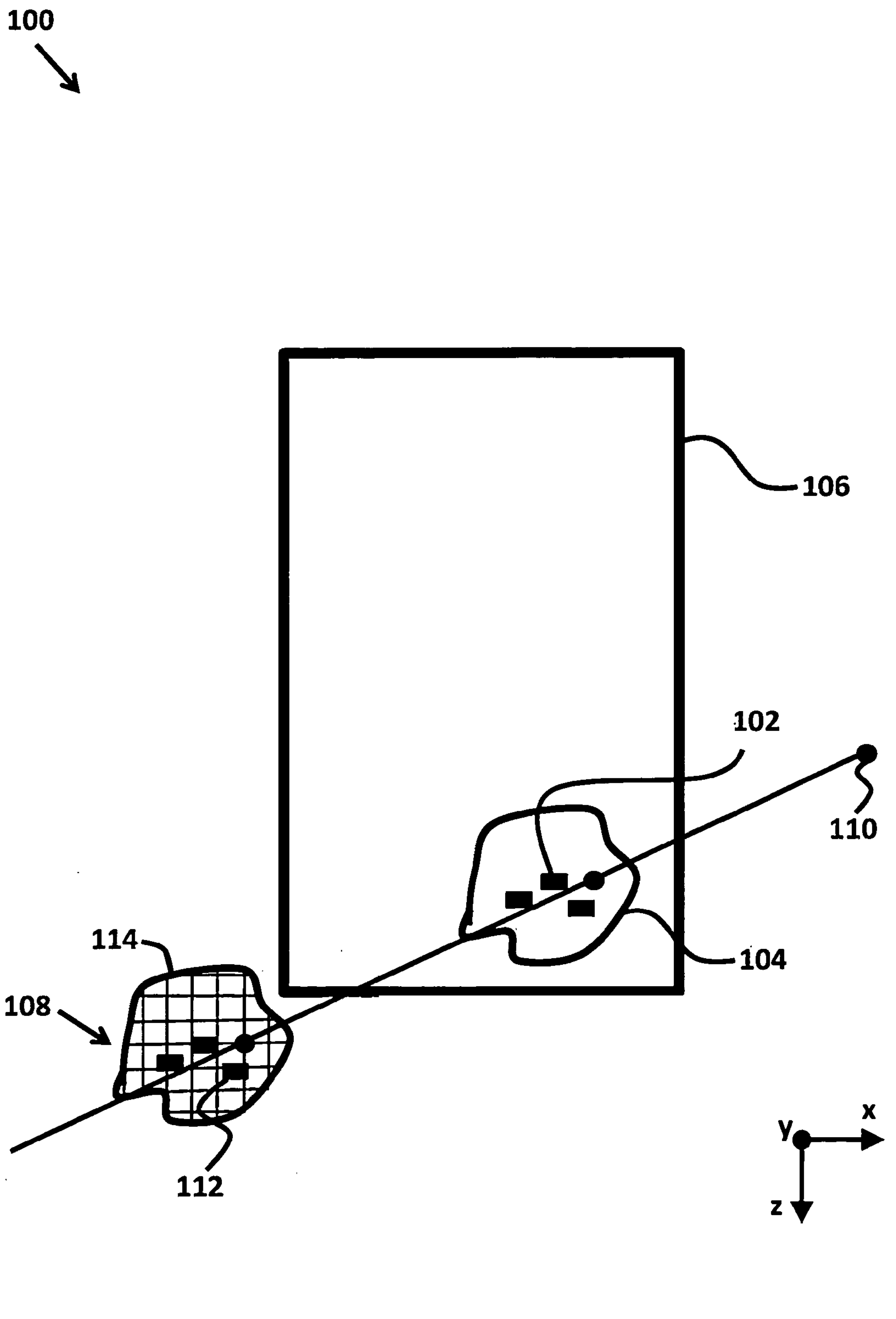
FIG. 1 shows a schematic of fiducial-based monitoring of tumor motion, according to one embodiment of the invention.
Figure 2:
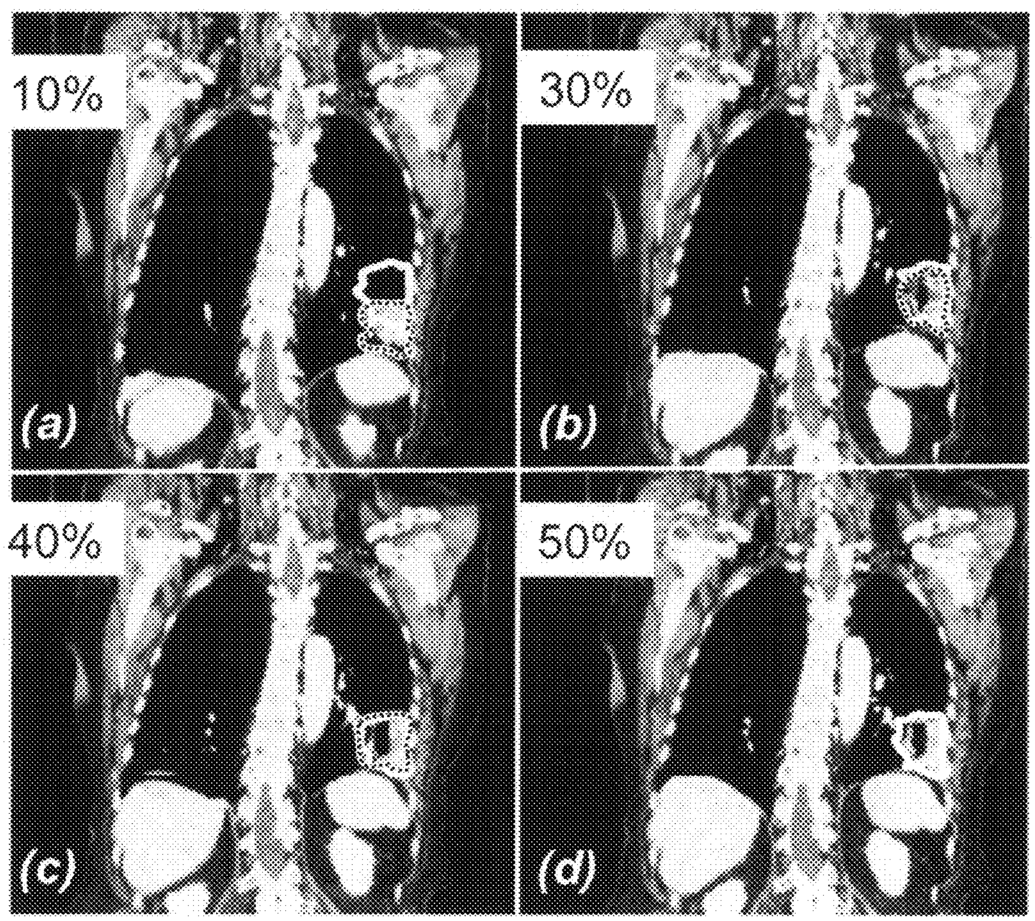
FIGS. 2*a*-2*d* show a lung patient CT images at 10%, 30%, 40%, and 50% phases provided for exemplary case studies, according to one embodiment of the current invention.
Figure 3:
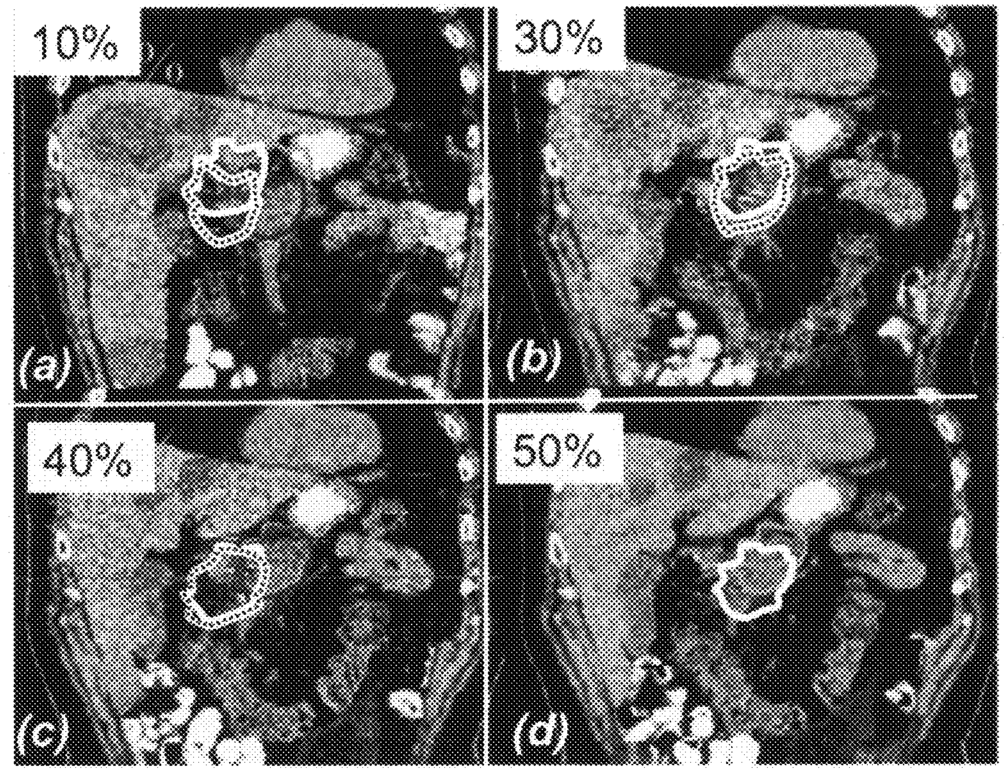
FIGS. 3*a*-3*d* show pancreas patient CT images at 10%, 30%, 40%, and 50% phases provided for exemplary case studies, according to one embodiment of the current invention.

The current invention includes a method of 4D inverse planning that is capable of controlling the appearance of the implanted fiducial(s) in segmented IMRT fields for cine MV or combined MV/kV image-guided IMRT. The method includes enhancing the visibility of the implanted fiducial(s) in 4D IMRT inverse planning to derive a set of time-resolved (or phase-tagged) MLC segments to cater for the motion of the patient anatomy extracted from the emerging 4D images. The invention provides a method to optimize the shapes and weights of all the segments for each incident beam, with the fiducial(s) being forced/encouraged to be inside the segmented fields. In one aspect, the invention provides a system that is modeled by a quadratic objective function with inclusion of a hard/soft constraint characterizing the authors' level of preference for the fiducial(s) to be included in the segmented fields. According to one embodiment of the invention, a simulated annealing algorithm is employed to optimize the system. The proposed technique is demonstrated using two exemplary clinical cases. A segment-based inverse planning framework for 4D radiation therapy, capable of providing tempospatially optimized IMRT plans, is provided. Furthermore, using the described 4D optimization approach according to the current invention, it is demonstrated that the MLC blockage of the implanted fiducial(s) during the segmented delivery is avoided without severely compromising the final dose distribution. According to the invention, the visibility of implanted fiducials in 4D IMRT is improved without significantly deteriorating final dose distribution.

The goal of 4D IMRT inverse planning is to derive a set of time-resolved MLC segments to maximally compensate for the motion of the patient anatomy extracted from 4D images. While ideally a 4D IMRT plan yields the optimal cumulative dose distribution, a practical issue exists on how to ensure that the segmented IMRT dose is delivered to the target at the right position and right time. Monitoring the position of the implanted fiducial in real time represents a useful option to ensure appropriate 4D radiation therapy delivery. According to one aspect of the invention, the "visibility" of the implanted fiducials is greatly enhanced by introducing a fiducial constraint in the 4D inverse planning process. While the IMRT dose distribution with added physical constraints is degraded unsurprisingly, the degradation of plan quality is often not detrimental, especially when a soft constraint is employed. The current invention will be part of future 4D IMRT inverse planning when cine MV imaging is involved in fiducial tracking.

Two major but related components are considered in this discussion: (i) Incorporation of temporal variable into optimization or 4D inverse planning and (ii) enhancement of the fiducial visibility in the IMRT delivery. These two issues are addressed in different subsections below.

Regarding 4D inverse planning, a patient specific 4D model for improved therapeutics and opens the possibility of 4D IMRT is provided, in which the segments are optimized with respect to space and phase. In the following discussion the number of beam and their angles are specified empirically.

In the following examples, the motion is discretized into ten phases. For convenience, each beam has ten segments, each for a phase. A segment for a given gantry angle θ and a phase p is denoted by $a_{\theta,p}(w_{\theta p}, \{x^l_{\theta p}(A), x^l_{\theta p}(B)\})$, where $w_{\theta p}$ is the weight of the segment and $\{x^l_{\theta p}(A), x^l_{\theta p}(B)\}$ describes the coordinates of the $1^{th}$ MLC leaf pair of the segment.

The aim of 4D IMRT planning becomes finding the optimal shapes and weights of all segments. 4D inverse planning objective function is written as $$S(D_c) = \sum_{i=1}^{n_{struct}} \frac{1}{n_i^{voxel}} \left[ \sigma_{1,i} \sum_{n=1}^{n_i^{voxel}} H(D_i^{low} - D_c(n)) + \sigma_{2,i} \sum_{n=1}^{n_i^{voxel}} H\left(D_c(n) - D_i^{high}\right) \right] \times (D_c(n) - D_i^p)^2, \quad (1)$$

where $D_i^p$ is the prescription dose for the $i^{th}$ structure, $\sigma_{i,1}$ and $\sigma_{i,2}$ are weighting factors for overdosing and underdosing specific to structure i, and H(x) is the Heaviside step function (takes 1 for positive x and 0 otherwise). In this objective function, penalty goes to the voxels with dose D(n) higher than the upper bound or lower than the lower bound. The calculated dose distribution in Eq. (1) is a function of the shapes and weights of all segments. According to one embodiment, optimization of the objective function yields the optimal segment shapes and weights subject to physical constraints imposed by system hardware.

In the segment-based 4D treatment planning according to the invention, the dose to a voxel is a superposition of the doses from all phases and segments. For a given phase, the calculated dose distribution changes with segment shapes and weights, and the dose is computed by summing the contribution from each segment of each beam. When multiple phases are involved, a deformable registration model is used to track the movement of each voxel. By using 4D CT images and deformable registration, the voxel displacement vector field (DVF) $T_{p\to r}$ is obtained. A DVF describes the displacement of a voxel in a phase (p) with respect to the reference phase (r): $\Delta\vec{x}_{p\to r}=\vec{x}^{(p)}-\vec{x}^{(r)}$. The cumulative dose is expressed as $$D_c(n) = \sum_P T_{p\to r} \sum_\theta w_{a_{\theta p}} K_{a_{\theta p}}(n), \quad (2)$$

where $K_a(n)$ is the dose at a voxel n from the segment depicted by $a_{\theta p}$ with unit intensity. The DVF transforms the dose contribution computed in the $p^{th}$ phase into the dose in the rth (reference) phase.

According to the invention, the objective function defined in Eq. (1) is optimized by using a simulated annealing (SA) technique. Here, the segment shapes are initialized to conform to the projection of the target in the beam's eye view (BEV) at the corresponding phase of the breathing cycle. Equal weights are assigned to all segments initially. In each iteration of SA, a trial change of the segment shape and weight is introduced. The trial change is accepted or rejected according to a probability determined by two factors. One is a SA probability of rejecting a trial P, which is determined by the change of objective function ΔS and system temperature T:

$$P = \begin{cases} 0 & \text{if } \Delta S < 0 \\ 1 - \exp(\Delta S / T) & \text{otherwise.} \end{cases} \quad (3)$$

The other is whether the segment blocks a fiducial or not. The composite rejecting probability of a trial segment is given by $$P' = P + \xi(1 - P), \quad (4)$$

where ξ is a coefficient determined by the fiducial blockage status (details are given below). If the trial segment shape is not accepted, a new trial segment will be followed.

According to the invention, a built-in mechanism for avoiding MLC blockage of the fiducials in the delivery segments is introduced to the 4D inverse treatment planning strategy. FIG. 1 shows a schematic of fiducial-based monitoring of tumor motion 100. Shown is an example of three fiducials 102 implanted in the target 104 of a body 106. The implanted fiducials 102 can generally be blocked by the segmented fields 108 of an IMRT plan. A beam source 110 directed through the target 104 generates the projection points 110 of the fiducials 102 in BEV 112.

According to the current invention, to discourage or prevent this from happening, a penalty scheme is introduced if any of the fiducials is blocked by a segmented field. The penalty is tuned and controlled by a coefficient ξ introduced in the composite rejecting probability Eq. (4). If all the fiducials fall in the segmented field, there is no penalty during optimization, that is, ξ=0 in Eq. (4) and P' reduces to P. Otherwise, the penalty is imposed by assigning ξ a positive value. To be specific, both hard and soft constraints are considered here. In the case of hard constraint, ξ=1 and the composite probability P' is equal to unity. When the hard constraint is applied, a trial segment shape that blocks a fiducial is always rejected. For soft constraint, ξ is set to be 0.5 and the probability of rejecting a trial segment shape is increased to P'=0.5(P+1). The construction of rejecting probability for a trial segment here is somewhat empirical but serves the purpose of encouraging inclusion of implanted fiducials in the MLC segments.

An exemplary case study is provided, where two patients' 4D CT data, one lung cancer (FIG. 2) and one pancreas cancer (FIG. 3), are used to illustrate the performance of the proposed technique. FIGS. 2*a-d* show a lung patient CT images at 10%, 30%, 40%, and 50% phases, respectively. The contour of the target is plotted on the CT image of the corresponding phase. The 50% phase target contour is also overlaid onto 10%, 30%, and 40% phases. FIGS. 3*a*-3*d* show pancreas patient CT images at 10%, 30%, 40%, and 50% phases, respectively. The contour of the target is plotted on the CT image of the corresponding phase. The 50% phase target contour is also overlaid onto 10%, 30%, and 40% phases.

In these examples, the respiratory cycle is divided into ten phases of equal duration, with phase 10% representing the end of inhalation and phase 50% the end of exhalation. The contours of regions of interest (ROIs) are delineated on the 50% phase (reference phase).

Figure 4:
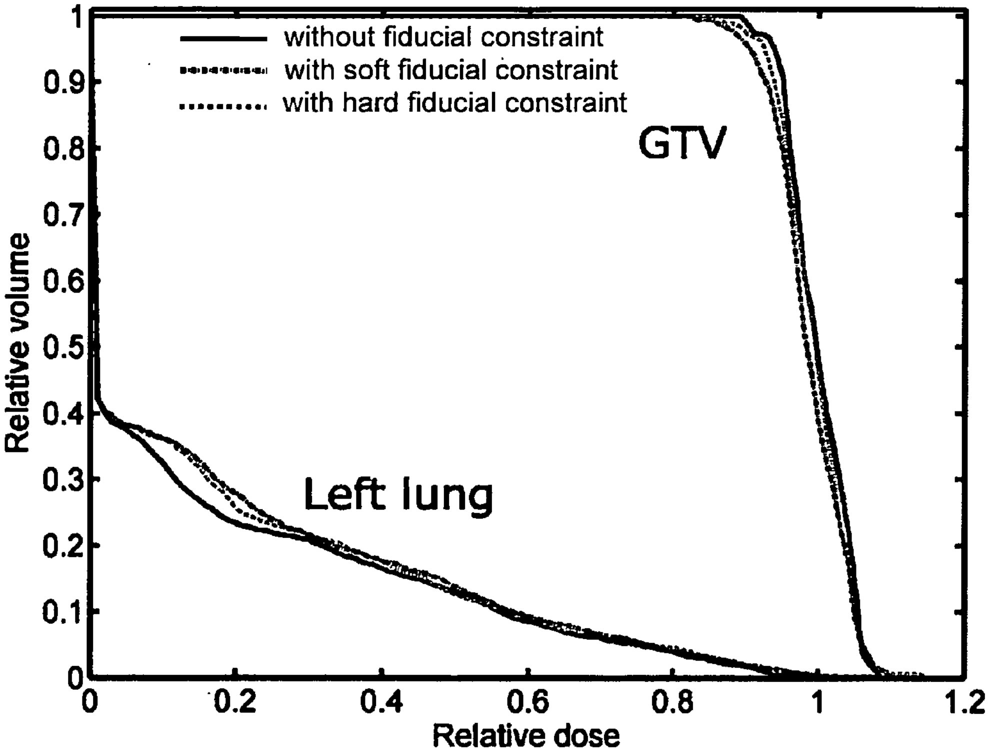
FIG. 4 shows DVHs for target and left lung for the lung cancer patient.

The ROI contours on the other nine phases of the 4D CT data are automatically generated using the deformation field obtained by using deformable registration. Five 6 MV beams (80°, 150°, 250°, 300°, 350°) are used for the lung IMRT and six 6 MV beams (80°, 120°, 150°, 200°, 240°, 290°) are used for pancreas IMRT. FIG. 4 shows DVHs for target and left lung for the lung cancer patient. The solid, dash, and dash-dot curves represent the results obtained by the 4D IMRT plan without fiducial constraint, with soft fiducial constraint, and with hard fiducial constraint, respectively.

Figure 5:
FIGS. 5*a*-5*c* show dose distributions in transverse plane of the lung cancer patient subject to the three different fiducial constraint conditions, according to embodiments of the current invention.

Regarding the results of the example for the lung patient, the dose-volume histograms (DVHs) and dose distributions resulting from the 4D inverse planning with or without soft/hard fiducial constraints are shown in FIGS. 4 and 5, respectively. When the fiducials are forced to be seen, slight degradation of the dose distributions are observed in both target coverage and OAR sparing. The target mean dose is lowered from 59.7 to 59.3 Gy/58.9 Gy when the soft/hard fiducial constraint is applied. The standard deviation (STD) of target dose is increased from 2.5 to 2.8 Gy/2.9 Gy for the two constrained cases. Simultaneously, the target dose level covering 90% of the target volume (D90) is decreased from 95% to 94% and 93%, respectively. These results indicated that the use of fiducial constraints leads only to moderate change in the final dose distribution. Not surprisingly, the hard constraint degrades the plan more as compared to that of the soft constraint. The constraints also slightly increase the left lung dose. However, it should be noted that the lung volume receiving 25% or higher dose is essentially not changed regardless of what type of constraint is used, as is clearly seen by comparing the stomach fractional volume with 24 Gy or more dose (V24 value) for the three plans. The dose degradation mainly happens in the low dose region (<24%). The stomach fractional volumes with 10 Gy or more dose (V10 value) for the three plans are 25.3%, 28.9%, and 30.0%, respectively. Note that the parameters characterizing the plans, including the mean dose, STD, D90 for target, and V10 and V24 for the left lung, are summarized in Table I for the three plans.

TABLE I

Summary of the 4D lung IMRT plan statistics for the three different kinds of fiducial constraints.

| Lung | Free | Soft | Hard |
|---|---|---|---|
| GTV mean dose (Gy) | 59.7 | 59.3 | 58.9 |
| GTV dose STD (Gy) | 2.5 | 2.8 | 2.9 |
| GTV D90 (%) | 95.0 | 94.0 | 93.0 |
| LT lung V10 (%) | 25.3 | 28.9 | 30.0 |
| LT lung V24 (%) | 16.6 | 17.6 | 17.6 |

FIGS. 5*a*-5*c* show dose distributions in transverse plane of the lung cancer patient subject to the three different fiducial constraint conditions. The dose distributions obtained by the plans without fiducial constraint, with soft fiducial constraint and with hard fiducial constraint are shown from FIGS. 5*a*-5*c*.

Figure 6:
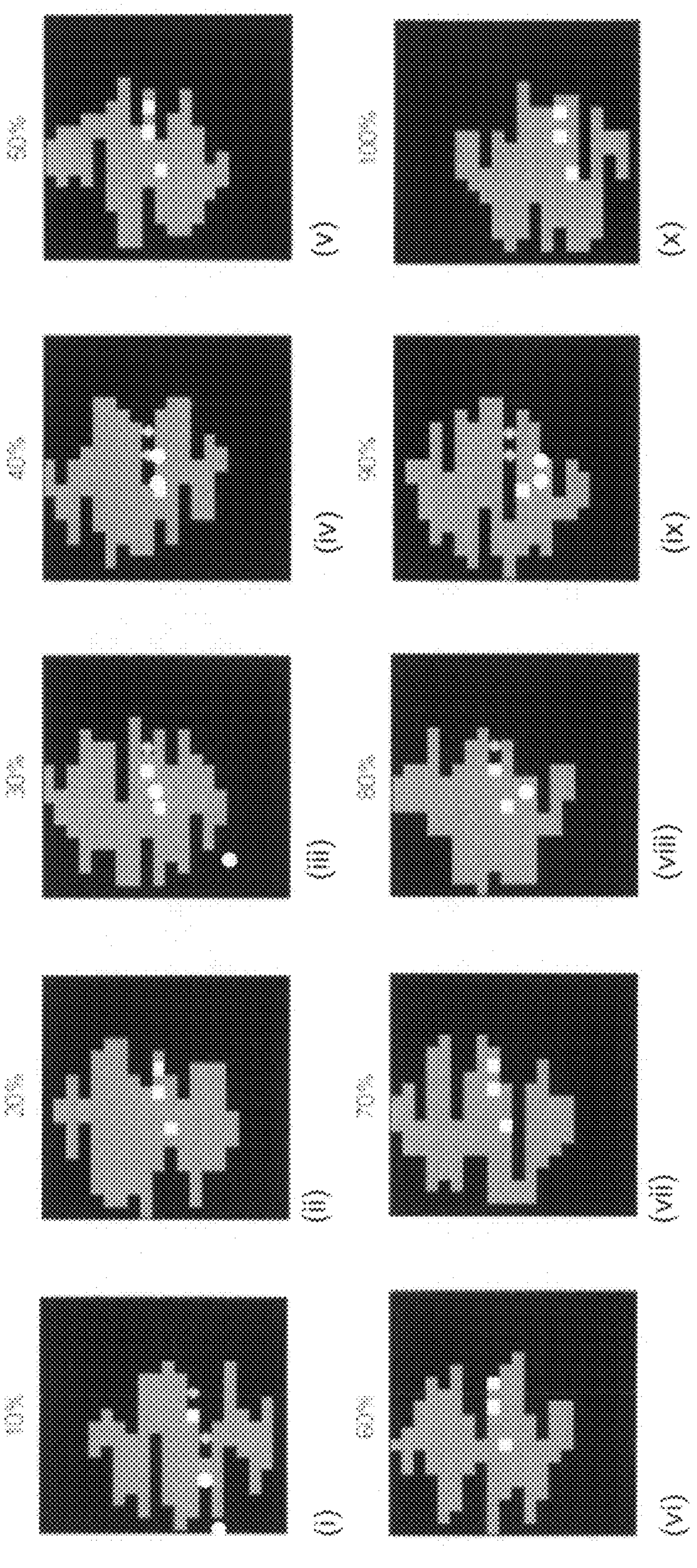
FIGS. 6*a*(i)-6*c*(x) show segmented fields of the first beam (80° gantry angle) for the lung 4D IMRT plan, according to embodiments of the current invention.
Figure 6:
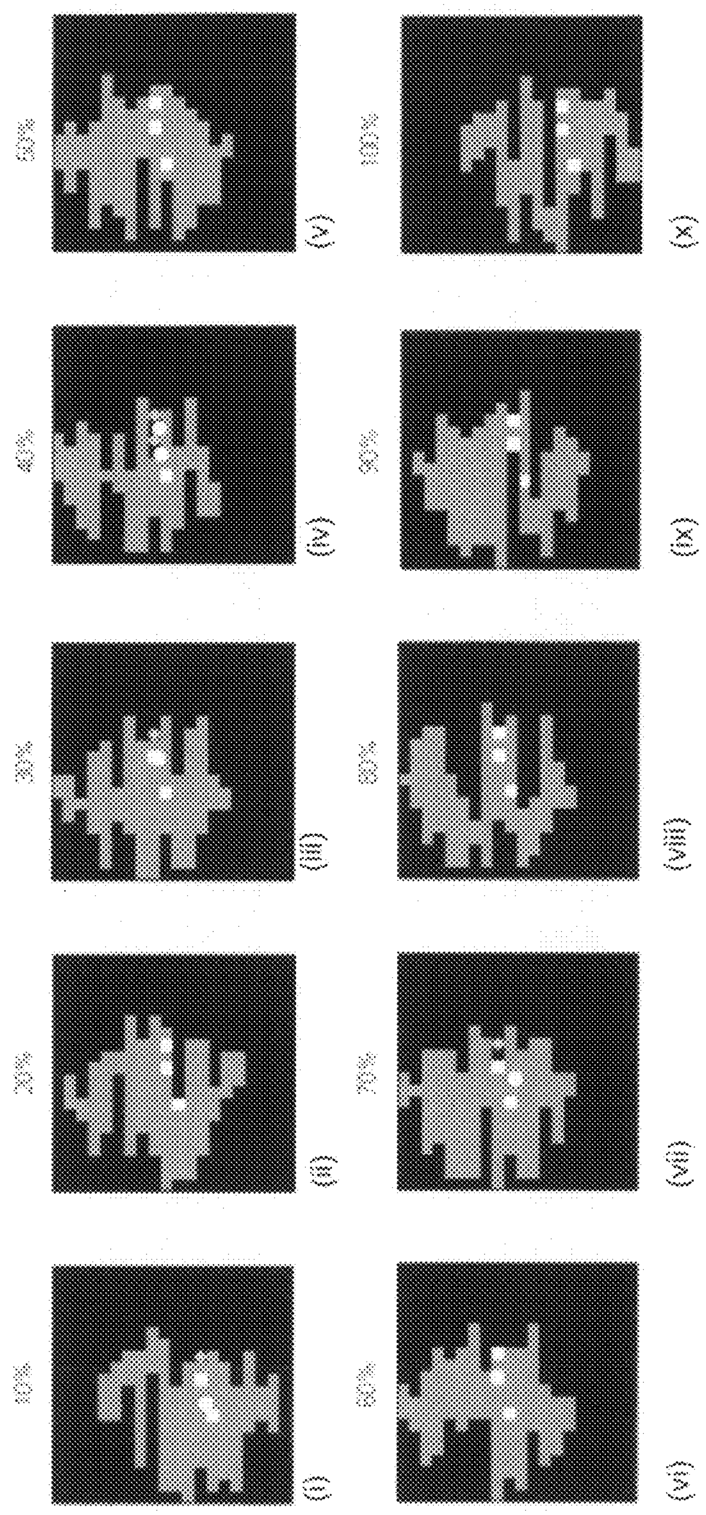
Figure 6:
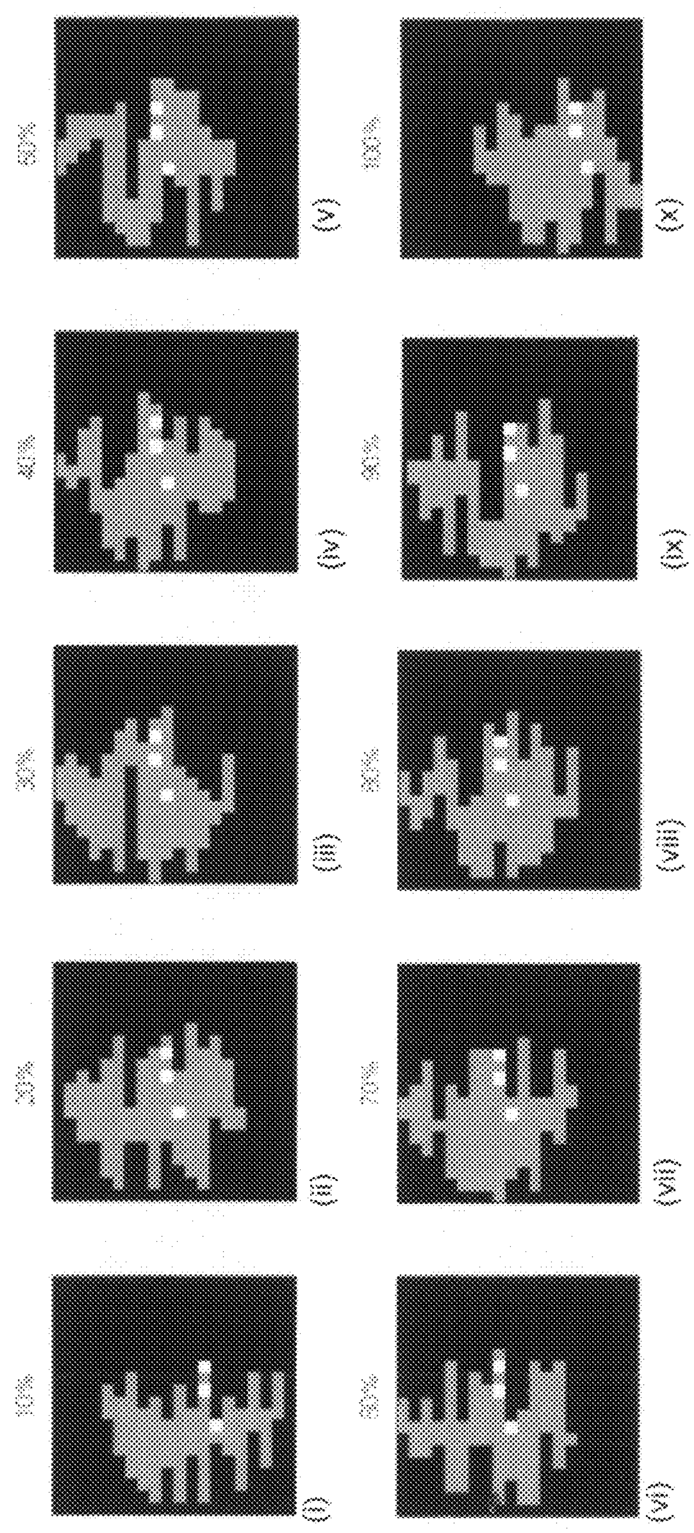

The optimized segment shapes of the first beam (80° gantry Angle) for the three plans are shown in FIG. 6. The phase number of each segment is indicated on the top of the segmented field shape. As seen from the upper panel of FIG. 6, at least one fiducial is located in five out of ten segments when no fiducial constraint is applied. With the use of soft constraint, the number is increased to 6 for this beam. The fiducials appear in all ten segments when hard constraint is applied. Overall, for the five beams, the number of segment that blocks at least one fiducial is 52%, 32%, and 0% for plans obtained with no fiducial constraint, with soft fiducial constraint, and with hard fiducial constraint, respectively. In the present definition of fiducial constraint, (is a tunable parameter (0<ξ≤1) that controls the degree of the constraint. The current selection is ξ=0.5 for soft constraint.

FIGS. 6*a*(i)-6*c*(x) show segmented fields of the first beam (80° gantry angle) for the lung 4D IMRT plan. The panels 6*a*(i)-6*a*(x) represent the segmented fields resulting from the 4D IMRT plan without fiducial constraint. The panels 6*b*(i)-6*b*(x) and 6*c*(i)-6*c*(x) represent the results from the 4D IMRT plan with soft and hard fiducial constraint, respectively. The squares are the implanted fiducials. The circles indicate the blocked fiducials.

It is interesting that, in all three cases, the apertures for the 10% and 100% phases move down by about 2.5 cm relative to the apertures irradiating the expiration phase (50% Phase). This segment shift is a direct consequence of the tumor motion. Indeed, by inspiration of the 4D CT images of the patient, it can be seen that the motion of the tumor at this phase is about 2.3 cm in superior-inferior (SI) direction (FIGS. 2*a*-2*d*). In a sense, the 4D IMRT plan tracks the tumor motion by shifting the apertures.

Figure 7:
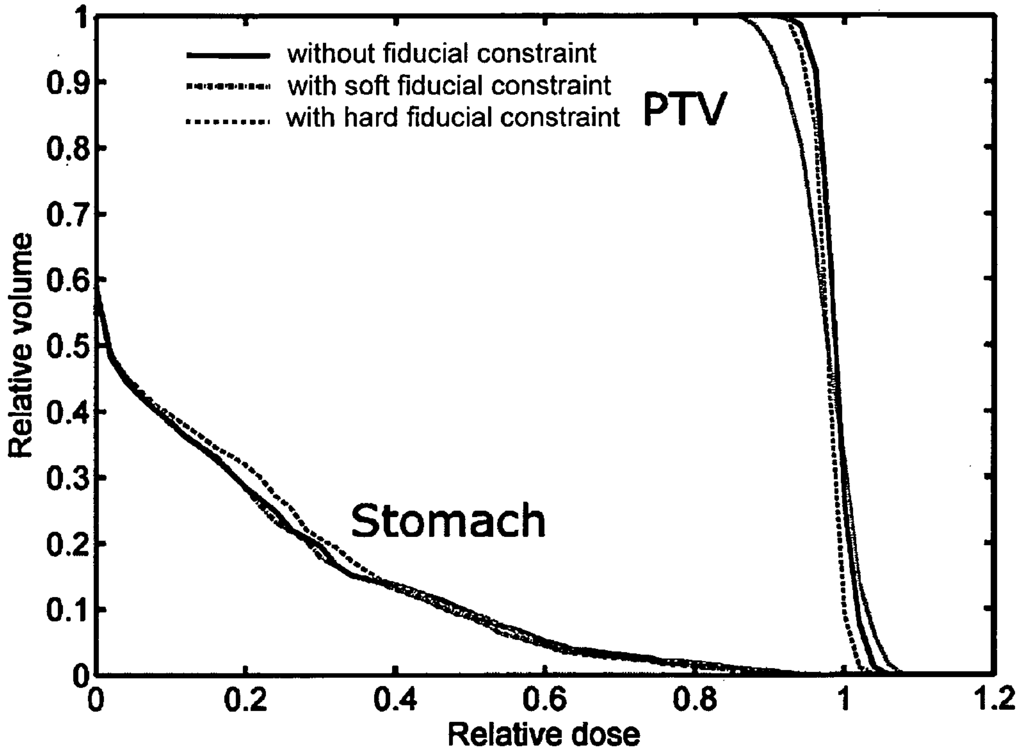
FIG. 7 shows DVHs for target and stomach for the pancreas cancer patient, according to one embodiment of the current invention.
Figure 8:
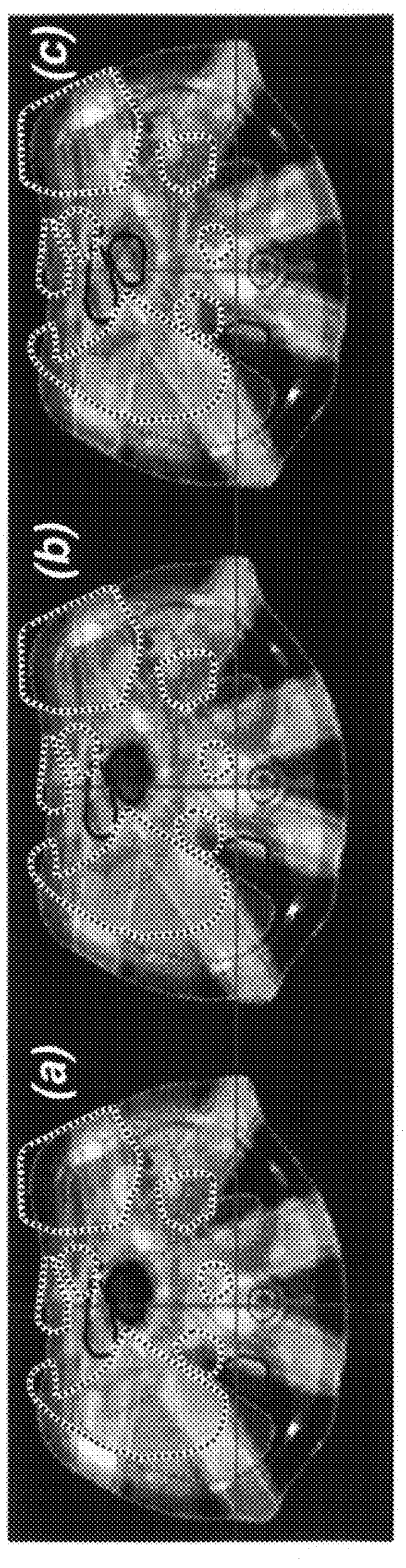
FIGS. 8*a*-8*c* show dose distributions in transverse plane of the pancreas cancer patient subject to the three different fiducial constraint conditions, according to one embodiment of the current invention.

Regarding the results for a pancreas patient, DVHs and dose distributions resulting from the 4D inverse planning with no fiducial constraint and with soft or hard fiducial constraints are shown in FIG. 7 and FIGS. 8*a*-8*c*, respectively. FIG. 7 shows DVHs for target and stomach for the pancreas cancer patient. The solid, dash, and dash-dot curves represent the results obtained by the 4D IMRT plan without fiducial constraint, with soft fiducial constraint, and with hard fiducial constraint, respectively. FIGS. 8*a*-8*c* show dose distributions in transverse plane of the pancreas cancer patient subject to the three different fiducial constraint conditions. The dose distributions obtained by the plans without fiducial constraint, with soft fiducial constraint, and with hard fiducial constraint are shown from FIGS. 8*a* to 8*c*. In the dose distribution shown in FIGS. 8*a*-8*c*, low dose is observed within the target in the plan with the hard fiducial constraint. The target mean dose is degraded from 59.7 to 59.1 Gy/51.1 Gy when a soft/hard fiducial constraint is applied. The STD of target dose is increased from 2.9 to 2.9 Gy/3.3 Gy for the two constrained cases. Simultaneously, the target dose level covering 90% of the target volume (D90) is decreased from 93% to 92% and 91%, respectively. These results indicated that the use of fiducial constraints leads only to moderate change in the final dose distribution. The dose distribution in the stomach is slightly worsened by the inclusion of fiducial constraints. The degradation happens mainly in the low dose region. The V10 values are 30.3%, 31.6% and 33.9% for plans without fiducial constraints and with soft or hard constraints, respectively. The V24 values are 11.5%, 13.1%, and 13.2% for the three plans. For the region with a dose of 40% or higher, little change is observed.

The plan statistics for the three scenarios are summarized in Table II. Similar to the previous case, only slight degradation in treatment plan is seen when a fiducial constraint is applied.

TABLE II

Summary of the 4D pancreas IMRT plan statistics for the three different kinds of fiducial constraints.

| Pancreas | Free | Soft | Hard |
|---|---|---|---|
| GTV mean dose (Gy) | 59.7 | 59.1 | 59.1 |
| GTV dose STD (Gy) | 2.9 | 2.9 | 3.3 |
| GTV D90 (%) | 93.0 | 92.0 | 91.0 |
| Stomach V10 (%) | 30.3 | 31.6 | 33.9 |
| Stomach V24 (%) | 11.5 | 13.1 | 13.2 |

Figure 9:
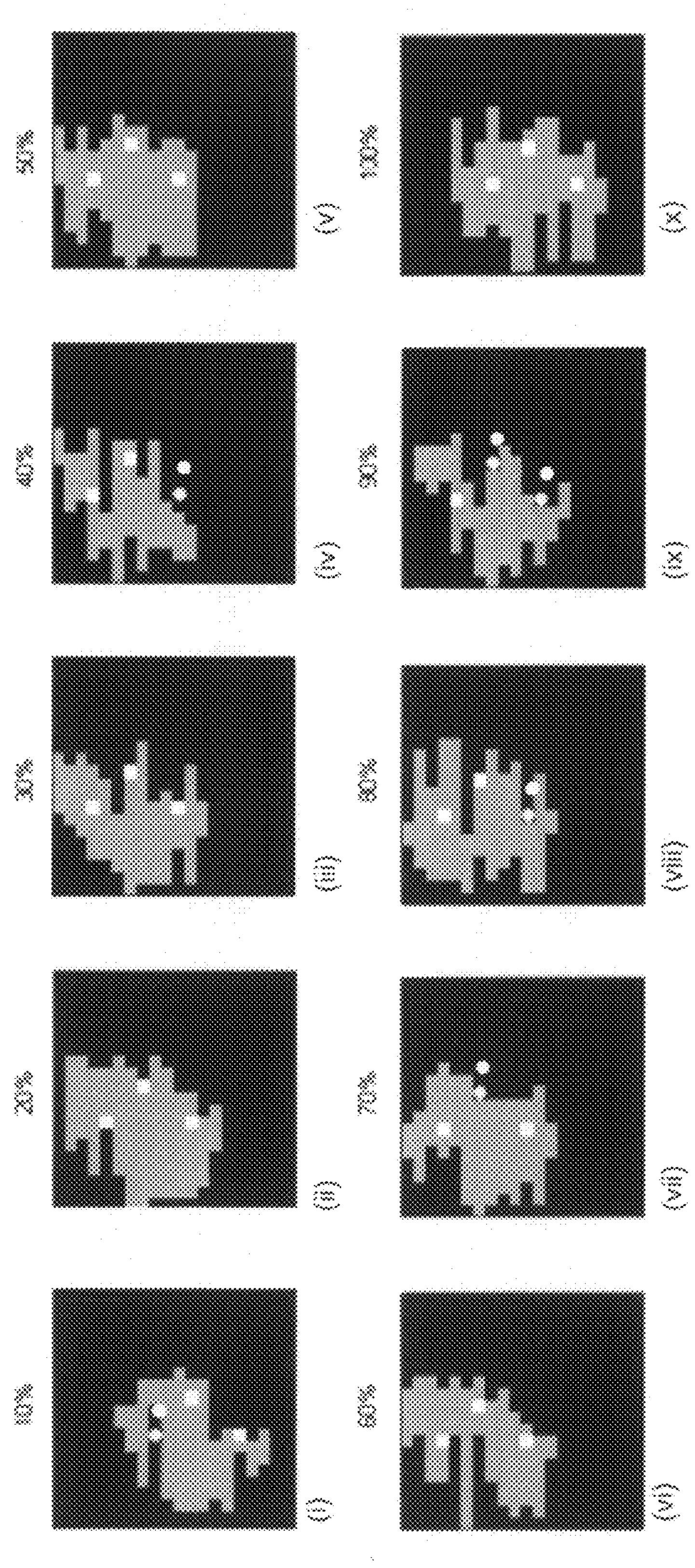
FIGS. 9*a*(i)-9*c*(x) show the optimal segment shapes of the first beam (80° gantry angle) for the three plans (constraint-free, with soft fiducial constraint, or with hard fiducial constraint), according to one embodiment of the current invention.
Figure 9:
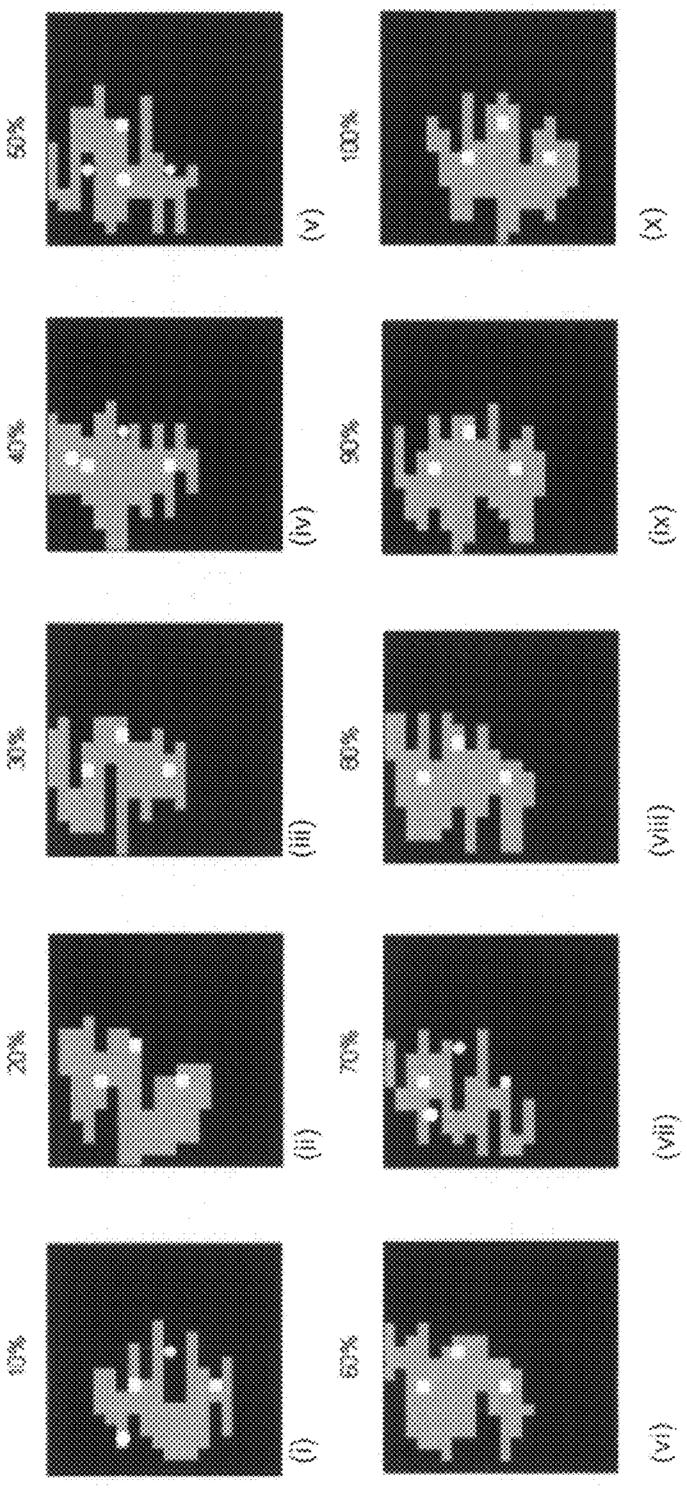
Figure 9:
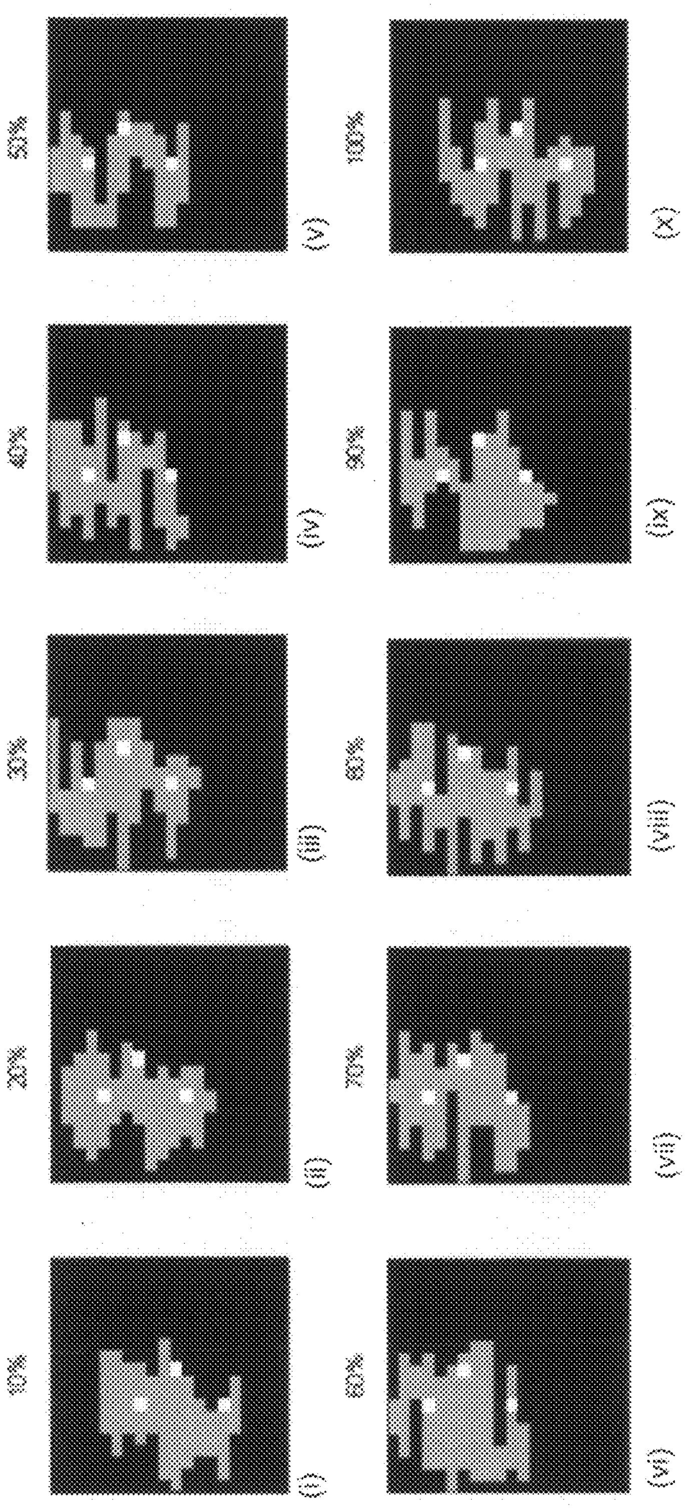

FIGS. 9*a*(i)-9*c*(x) show the optimal segment shapes of the first beam (80° gantry angle) for the three plans (constraint-free, with soft fiducial constraint, or with hard fiducial constraint). The phase number of each segment is indicated on the top of the segmented field shape. As seen from FIGS. 9*a*(i)-9*c*(x), five out of ten segments contain the three fiducials when no fiducial constraint is applied. With soft constraint, the number of the segmented fields blocking at least one fiducial is decreased to 4 for this beam. No fiducials show up in all the segments with the use of hard constraint. For the six beams, overall percentage of fiducial(s) blockage is 48%, 37%, and 0%, respectively, for the three scenarios.

It is important to note that the inverse planning procedure described above is based on the patient's simulation 4D CT. In reality, patient's breathing pattern changes from time to time, which may change the relative position of the fiducials and the MLC segments and cause a problem during the actual IMRT delivery. A straightforward approach to prevent this from happening is to introduce a margin for each implanted marker so that the whole motion range of the fiducial is considered during inverse planning. The size of the margin depends on the specifics of delivery. For respiration-gated delivery, for example, the margin needs only to cover the residual motion range of the fiducial for the specific gating window. Of course, patient setup inaccuracy should also be considered when specifying a margin to the fiducial. A more advanced approach that one can take is to include a probability model of the fiducial motion derived from 4D simulation CT. The method described in this work should be extendable to deal with the fiducial margin or probability distribution discussed here.

In summary, a segment-based inverse planning framework for 4D radiation therapy has been described. By extending inverse planning from 3D to 4D, a tempospatially optimized IMRT plan can be achieved. 4D IMRT allows us to fully consider the patient's anatomical change during respiration and maximize the IMRT delivery efficiency. Furthermore, it is demonstrated that the MLC blockage of the implanted fiducial(s) during the segmented delivery can be partially or completely avoided without severely compromising the final dose distribution. 4D inverse planning with enhanced fiducial(s) visibility provides a basis for future cine MV or hybrid kV/MV imaging guided 4D IMRT.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method for radiation treatment comprising computing a radiation treatment plan and delivering beams to a target in accordance with said radiation treatment plan, wherein computing said radiation treatment plan comprises introducing a penalty in an inverse planning objective function optimization calculation to discourage or avoid blockage of one or more fiducials in optimized multi-leaf collimator (MLC) apertures, wherein for a given gantry angle θ and phase p, a weight $w_{\theta p}$ is provided for a phase-segment, wherein said radiation treatment plan optimizes shapes and weights of all said MLC aperture shapes.

2. The method of claim 1, wherein said penalty comprises a hard penalty or a soft penalty, wherein said hard penalty avoids blockage of said fiducial, wherein said soft penalty discourages blockage of said fiducial.

3. The method of claim 1, wherein said fiducials are selected from the group consisting of an implanted fiducial, a skin marker, a tissue feature point, and a tissue region.

4. The method of claim 1, wherein said MLC aperture comprises segment aperture shapes that conform to a projection of said target in a beam's eye view of said delivery beam, wherein said shapes are optimized according to a space and phase of a breathing cycle in a patient.

5. The method of claim 1, wherein motion of said fiducials is discretized into phase-segments.

6. The method of claim 5, wherein a radiation dose provided to a voxel comprises a superposition of said radiation doses and phase-segments from all said MLC segments, wherein said dose is determined by summing a contribution from each said MLC segment for each said beam.

7. The method of claim 1, wherein said MLC aperture comprise MLC segments, wherein a calculated dose distribution is a function of said MLC aperture shapes and weights of all said MLC segments.

8. The method of claim 1, wherein said penalty is dedicated to a voxel with a dose higher than a designated upper bound or dedicated to a voxel with a dose lower than a designated lower bound.

9. The method of claim 1, wherein said inverse planning objective function is optimized using a simulated annealing (SA) technique, wherein in each iteration of said SA a trial change of said aperture and trial change of a weight of said penalty is introduced, wherein said trial change is accepted or rejected according to a probability determined by an SA probability and whether an MLC segment blocks said fiducial or not.

10. The method of claim 1, wherein said inverse planning objective function is optimized using an optimization function.

11. The method of claim 1, wherein said inverse planning objective function comprises a 4D inverse planning objective function.

12. The method of claim 1, wherein said penalty has a value in a range of 0to 1.

* * * * *

UNITED STATES PATENT AND TRADEMARK OFFICE

CERTIFICATE OF CORRECTION

PATENT NO. : 9,227,085 B2
APPLICATION NO. : 12/932666
DATED : January 5, 2016
INVENTOR(S) : Yunzhi Ma It is certified that error appears in the above-identified patent and that said Letters Patent is hereby corrected as shown below:

In the specification

In column 1, lines 14 thru 21, change

"STATEMENT OF GOVERNMENT SPONSORED SUPPORT
This invention was made with Government support under contract 5R01CA104205 awarded by National Cancer Institute, and under contract W81XWH05-1-0041 awarded by Department of Defense. The Government has certain rights in this invention."

to

STATEMENT OF GOVERNMENT SPONSORED SUPPORT
This invention was made with Government support under contract W81XWH-05-1-0041 awarded by the Department of Defense and under contract CA104205 awarded by the National Institutes of Health. The Government has certain rights in the invention.

Signed and Sealed this
Fifth Day of April, 2016

Michelle K. Lee
*Director of the United States Patent and Trademark Office*